(12) United States Patent
Greatbatch et al.

(10) Patent No.: US 7,136,701 B2
(45) Date of Patent: Nov. 14, 2006

(54) HYBRID BATTERY POWER SOURCE FOR IMPLANTABLE MEDICAL USE

(75) Inventors: Wilson Greatbatch, Akron, NY (US); Jeffrey Deal, Clarence, NY (US)

(73) Assignee: GentCorp Ltd., Lancaster, NY (US)

( * ) Notice: Subject to any disclaimer, the term of this patent is extended or adjusted under 35 U.S.C. 154(b) by 240 days.

(21) Appl. No.: 10/727,349

(22) Filed: Dec. 3, 2003

(65) Prior Publication Data

US 2004/0158296 A1    Aug. 12, 2004

Related U.S. Application Data

(63) Continuation-in-part of application No. 10/407,916, filed on Apr. 4, 2003, now Pat. No. 7,020,519, which is a continuation-in-part of application No. 10/350,921, filed on Jan. 24, 2003, now Pat. No. 6,909,915.

(51) Int. Cl.
  *A61N 1/40* (2006.01)
(52) U.S. Cl. ................... 607/5; 607/29; 320/103
(58) Field of Classification Search ........... 607/5, 607/29, 34; 320/103–104
  See application file for complete search history.

(56) References Cited

U.S. PATENT DOCUMENTS

| | | | |
|---|---|---|---|
| 3,941,135 A | 3/1976 | von Sturm et al. | 128/419 |
| 3,959,706 A | 5/1976 | Mabuchi et al. | 320/2 |
| 4,119,103 A | 10/1978 | Jirak | 128/419 |
| 4,548,209 A | 10/1985 | Wielders et al. | 128/419 |
| 4,736,150 A | 4/1988 | Wagner | 320/21 |
| 5,235,979 A | 8/1993 | Adams | 607/5 |
| 5,332,631 A | 7/1994 | Abraham et al. | 429/48 |
| 5,372,605 A | 12/1994 | Adams et al. | 607/5 |
| 5,383,907 A | 1/1995 | Kroll | 607/5 |
| 5,405,363 A | 4/1995 | Kroll et al. | 607/5 |
| 5,407,444 A | 4/1995 | Kroll | 607/5 |
| 5,458,997 A | 10/1995 | Crespi et al. | 429/219 |
| 5,620,464 A | 4/1997 | Kroll et al. | 607/5 |
| 5,674,248 A | 10/1997 | Kroll et al. | 607/5 |

(Continued)

FOREIGN PATENT DOCUMENTS

WO    WO9622811    8/1996

OTHER PUBLICATIONS

"Simulation of capacity fade in lithium-ion batteries"; R. Spotnitz; Journal of Power Sources 113 (2003) 72-80; 9 pages.

(Continued)

*Primary Examiner*—Mark Bockelman
(74) *Attorney, Agent, or Firm*—Walter W. Duft

(57) ABSTRACT

A hybrid battery power source for implantable medical use provides a generally constant low internal resistance during discharge and avoids voltage delays of the type that develop as a result of run down-induced resistance increase in Li/SVO cells. The hybrid battery power source utilizes two batteries or cells, one being a primary cell of relatively high energy density and the other being a secondary cell of relatively low internal resistance that is rechargeable. The primary and secondary cells are connected in a parallel arrangement via a voltage boost/charge control circuit that is powered by the primary cell and adapted to charge the secondary cell while limiting charge/discharge excursions thereof in a manner that optimizes its output for high energy medical device use. The energy storage capacitors of the medical device in which the hybrid battery power source is situated are driven by the secondary cell. The primary cell is used to as an energy source for recharging the secondary cell.

30 Claims, 7 Drawing Sheets

BATTERY A

BATTERY B

U.S. PATENT DOCUMENTS

| | | | |
|---|---|---|---|
| 5,836,973 A | 11/1998 | Kroll | 607/5 |
| 6,180,283 B1 | 1/2001 | Gan et al. | 429/215 |
| 6,204,634 B1 | 3/2001 | Zimmerman et al. | 320/128 |
| 6,245,464 B1 | 6/2001 | Spillman et al. | 429/332 |
| 6,385,056 B1 | 5/2002 | Gucyski | 363/15 |
| 6,426,628 B1 | 7/2002 | Palm et al. | 324/427 |
| 6,444,360 B1 | 9/2002 | Gan et al. | 429/215 |
| 6,549,807 B1 | 4/2003 | Kroll | 607/34 |
| 6,552,511 B1 | 4/2003 | Fayram | 320/103 |
| 2003/0155887 A1 | 8/2003 | Bourilkov et al. | 320/104 |

OTHER PUBLICATIONS

"Calendar and cycle-life studies of advanced technology development program generation 1 Lithium-ion batteries" R.B. Wright et al.; Journal of Power Sources 110 (2002) 445-470; 26pages.

"Improve Battery Performance with Proper Charging methods"; Isidor Buchmann; Medical Electronics Manufacturing Fall 2003; 4 pages.

HYBRID BATTERY POWER SOURCE FOR IMPLANTABLE MEDICAL USE

CROSS-REFERENCE TO RELATED APPLICATIONS

This application is a continuation-in-part of U.S. patent application Ser. No. 10/407,916, filed on Apr. 4, 2003 now U.S. Pat. No. 7,020,519 and entitled "Hybrid Battery Power Source For Implantable Medical Use," which is a continuation-in-part of U.S. patent application Ser. No. 10/350,921, filed on Jan. 24, 2003 now U.S. Pat. No. 6,909,915 and entitled "Hybrid Battery Power Source For Implantable Medical Use."

BACKGROUND OF THE INVENTION

1. Field of the Invention

The present invention relates to improvements in the performance of implantable defibrillators, implantable cardioverter-defibrillators (ICDs) and other battery powered medical devices designed to provide high energy electrical stimulation of body tissue for therapeutic purposes.

2. Description of Prior Art

High energy battery powered medical devices, such as implantable defibrillators and ICDs, are designed to produce a strong electrical shock to the heart when called upon to correct the onset of tachyarrhythmia. The shock is produced by one or more energy storage capacitors that have been charged to a high voltage by the device's battery power source. The power source is typically a lithium/silver vanadium oxide (Li/SVO) battery or cell of the type disclosed in U.S. Pat. No. 5,458,997 of Crespi, and references cited therein. Crespi notes that the Li/SVO chemistry is useful for defibrillation applications because of its ability to produce pulses of energy that can charge the high voltage capacitors within the short time frame required by the device. In particular, the Li/SVO battery is typically called upon to charge the capacitors to deliver within 10 seconds or less a shock of up to 40 Joules. This must be done several times in succession if additional shocks are required. Unfortunately, as noted by Crespi, a Li/SVO cell can experience unpredictable resistance increase upon long-term discharge service. In particular, Li/SVO cells commonly have a two-stage run down with slightly different voltage plateaus at each stage. It is at the interval between the two plateaus where it is common to see the resistance increase described by Crespi. The problem is further explained in U.S. Pat. No. 6,426,628 of Palm et al. as being a transient phenomenon that occurs following a period of low current draw. When a load is reapplied (e.g., a defibrillation pulse is required), the resistance build-up temporarily prevents the cell from developing its full open circuit voltage potential. This condition, which is referred to as "voltage delay," continues for a brief period until the resistance diminishes back to some nominal level.

In many cases, the voltage delay experienced by a Li/SVO cell is significant enough to impair the cell's ability to charge the capacitors of a defibrillator or ICD in a timely manner. This may result, prematurely, in a decision being made that the Li/SVO cell has reached end of service (EOS) and needs to be explanted for replacement. In addition to the patient inconvenience and risk entailed by the explantation procedure, a significant portion of the capacity of the Li/SVO cell is needlessly rendered unavailable for long-term use. Even if it is not removed, the cell's operation is unpredictable, thus making any attempt to calculate the EOS point rather complicated.

Additional shortcomings in the application of Li/SVO cells have been previously identified in U.S. Pat. No. 5,674,248 of Kroll et al. A typical Li/SVO cell suitable for the described applications has an energy density of about 0.4 watt-hours per kilogram (Wh/kg) as compared to 0.8 Wh/kg for lithium/carbon monofluoride (Li/CFx) cells and 0.9 Wh/kg for lithium/iodide (Li/I) cells, the latter being used almost exclusively for implantable pacemakers. This energy density disadvantage requires the use of a battery with greater volume and weight than would otherwise be needed if the Li/CFx or Li/I cells could be used. However, the Li/CFx and Li/I cells are unsuitable for the described applications because they cannot support the rapid discharge rates required for charging the defibrillator capacitors. The Li/SVO cell has the added disadvantage of significantly higher cost when compared to the Li/CFx and Li/I chemistries.

The Kroll et al. patent proposes a staged energy concentration system for providing improved energy sources and device performance. A first energy stage utilizes a Li/CFx or Li/I battery to implement a primary power source. The first energy stage provides power to a second energy stage that utilizes either a lithium-based rechargeable secondary battery or a high energy density capacitor system. Energy is transferred at a low-rate from the first energy stage comprising the primary battery to the second energy stage comprising the rechargeable battery or the high energy density capacitor system. A trickle charge control circuit and a voltage doubler circuit are alternatively shown being interposed between the first and second energy stages. The second energy stage is rapidly discharged upon the detection of fibrillation to develop the high voltage charge needed for defibrillation therapy.

A shortcoming of the Kroll et al. high energy density capacitor system is the volume and number of capacitors needed for the second stage to support the storage of energy required, typically 200–300 Joules for a series of five therapeutic countershocks which might be required in a span of less than one minute. A shortcoming of the rechargeable battery system is that the lithium-based battery chemistries proposed for the secondary energy stage are not all suitable for the proposed application. Table 1 below sets forth the proposed chemistries. One is an $LiMnO_2$ system, but this is a primary system and is not suited to recharging. Another is an $LiSO_2$ system, but this operates with a sealed cell at a pressure of 3 to 6 atmospheres and is not suited for high-rate discharge applications. The remaining identified chemistries, namely $LiMoS_2$, $LiV_2O_5$, $LiTiS_2$, $LiV_6O_{13}$, $LiCuC_{12}$, NiCad, Alkaline and Lead acid, have not found wide acceptance in the implantable device market.

TABLE 1

| Second Stage Candidate Cells Identified in U.S. Pat. No. 5,674,248 | |
|---|---|
| Chemistry | Cell Voltage (VDC) |
| $LiMoS_2$ | 1.85 |
| $LiMnO_2$ | 3.0 |
| $LiV_2O_5$ | 2.8 |
| $LiTiS_2$ | 2.2 |
| $LiV_6O_{13}$ | 2.3 |
| $LiCuC_{12}$ | 3.2 |
| $LiSO_2$ | 3.1 |

A broader shortcoming is the failure of the Kroll et al. patent to identify a specific selection for a first stage battery and a configuration for the identified trickle charge control circuit or the voltage doubler circuit. A Li/I battery with a beginning of life open circuit voltage of 2.8 volts DC is identified within the disclosure as a potential candidate for the first energy stage. The output voltage of this cell falls to about 2.6 volts at EOS so the cell would be incapable of charging $LiMnO_2$, $LiV_2O_5$, $LiCuC_{12}$ and $LiSO_2$ cells unless the trickle charge control circuit utilized a means of increasing the first stage output voltage. This is clear because each of these cells has a higher operating voltage than the Li/I battery. The voltage doubler circuit is used in conjunction a first stage primary battery continuously recharging a second stage rechargeable battery. The Kroll et al. disclosure does not identify a method or means of controlling the flow of energy while recharging that is necessary to prevent damage to or catastrophic failure of the second stage cell or cells.

A need therefore exists for improvement in defibrillator/ICD battery power systems so to overcome the above-described deficiencies of the prior art.

SUMMARY OF THE INVENTION

The foregoing problems are solved and an advance in the art is provided by a novel hybrid battery power source for high energy battery powered medical devices, such as implantable defibrillators and ICDs. The hybrid battery power source has relatively constant charge time characteristics and is not affected by the voltage delay phenomenon associated with Li/SVO batteries. In addition, the hybrid battery power source provides a significant improvement in the stored energy density for an implantable power source that is suitable for high energy battery powered medical devices. Finally, the hybrid battery power source overcomes the limitations of staged energy conversion systems that have been previously disclosed.

In exemplary embodiments of the invention, the power source utilizes two batteries, each of which may comprise one or more cells. The first battery is a primary (nonrechargeable) battery of relatively high energy density. The second battery is a secondary (rechargeable) battery whose internal resistance is relatively low and stable over time. The primary battery and the secondary battery are connected in a parallel arrangement via a charge control circuit. The charge control circuit may include a voltage boost function and is adapted to limit the charge/discharge excursions of the secondary battery in a manner that optimizes its output for high energy medical device use.

It is therefore an object of the present invention to minimize the effect of the change in internal resistance as a battery for implantable medical use discharges during service.

A further object of the invention is to add a secondary power segment having low internal resistance and relatively constant terminal voltage to an implantable power source that will provide a source for rapid charging of energy storage capacitors used to deliver high energy impulses.

A still further object of the invention is to optimize the performance of a secondary power segment for use in a high energy medical device environment.

BRIEF DESCRIPTION OF THE DRAWINGS

The foregoing and other features and advantages of the invention will be apparent from the following more particular description of preferred embodiments of the invention, as illustrated in the accompanying Drawings in which.

DETAILED DESCRIPTION OF PREFERRED EMBODIMENTS

Introduction

Exemplary hybrid battery power sources for use with implantable defibrillators, ICDs and other high energy battery powered medical devices will now be described, together with an exemplary defibrillator that incorporates a hybrid battery power source therein. As indicated by way of summary above, the power source embodiments disclosed herein are characterized by having primary and secondary batteries. The primary battery has high energy density but typically will also have internal resistance that is relatively high, or which can increase significantly during discharge. Examples of this primary battery include the lithium-carbon monofluoride (Li/CFx) battery, the lithium-bromine chloride ($Li/BrCl_2$) battery, the lithium sulfuryl chloride ($Li/SO_2Cl_2$) battery, the lithium thionyl chloride ($Li/SOCl_2$) battery, the lithium-manganese dioxide battery ($Li/MnO_2$), and the lithium-silver vanadium oxide (Li/SVO) battery. The secondary battery is rechargeable and has low internal resistance that is relatively stable over time. It will typically also have relatively low energy density. Examples include the lithium-ion battery which typically utilizes lithium cobalt oxide and carbon or graphite. The primary and secondary batteries are electrically connected in an indirect parallel arrangement by means of a voltage boost/charge control circuit designed to optimize the performance of the secondary battery for high energy implantable medical use by limiting its maximum charge state and discharge excursions.

In this indirect parallel connection arrangement of the primary and secondary batteries, a voltage boost/charge control circuit is interposed to increase the voltage supplied by the primary battery and to control the flow of energy supplied by the primary battery to the secondary battery. This voltage boost/charge control circuit operates independently of primary battery run-down. For example, in a hybrid battery power source comprising an Li/CFx primary battery and a lithium-ion secondary battery interconnected by a voltage boost/charge control circuit, the principal energy supplied by the Li/CFx battery at about 2.8 volts can be increased to charge the lithium-ion battery to its normal open circuit voltage of about 4.0 volts, if desired. This charging voltage can be sustained throughout the life of the device even as the Li/CFx battery voltage falls during discharge to its typical end of life value of 2.0 volts. In this way, the primary battery is used as a long term energy supply to recharge the secondary battery for service when and if its voltage drops below the desired level. The voltage boost/charge control circuit also serves to limit the current drawn from the primary battery during defibrillatory charging, ensuring that virtually all of the energy is drawn from the secondary battery. This protects the primary battery from excessive high rate discharge that could lead to premature failure.

A third benefit provided by the voltage boost/charge control circuit is the regulation of the charging current and voltage that is supplied to the rechargeable secondary battery from the primary battery. In order to maximize secondary battery performance and minimize the risk of catastrophic cell failure, the voltage and current must be closely regulated throughout the life of both batteries, even as the primary battery voltage decays through normal discharge. In particular, the long-term performance of the secondary battery can be strongly influenced by the maximum state of charge (SOC) maintained on the battery and the discharge excursions that the battery experiences during use. For example, recharging and storing a lithium-ion secondary battery at or near 100% SOC and allowing significant discharge before the initiation of recharge can significantly increase the rate and extent to which the battery energy capacity irreversibly fades during battery service life. Irreversible capacity fade in a lithium-ion battery reduces its available energy output, which could decrease the number of high energy pulses available from an implantable medical device. Capacity fade has also been correlated to long term internal resistance increases. Though less than the internal resistance variance found in a typical Li/SVO primary cell designed for implantable medical use, the internal resistance increase of a lithium-ion secondary cell could nonetheless impact the high energy pulse generating cycle of an implantable medical device. As such, the voltage boost/charge control circuit is adapted to limit the maximum SOC and allowable discharge excursions of the secondary battery to optimal levels.

The hybrid power source embodiments disclosed herein can be designed for maximum service life by selecting the primary and secondary batteries so that the former provides most of the combined battery capacity while still allowing the latter to power a reasonable number of defibrillatory charging cycles prior to recharging, say 50 cycles. By way of example, the secondary battery could be selected to provide 10% of the total capacity of the power source, with the primary battery providing the remaining 90%.

If an implantable defibrillator or ICD is provided with one of the above-mentioned primary batteries and a lithium-ion secondary battery arranged in the manner disclosed herein, the lithium-ion battery will be the predominant energy source for charging the defibrillator's energy storage capacitors during the defibrillation cycle. Since this battery would always be charged to an energy capacity sufficient to support a predetermined number of defibrillatory cycles, the charge state and voltage of the primary battery would not be a factor in the ability of the device to quickly deliver defibrillation impulses. Thus, advantage can be taken of the superior energy density properties of the primary battery while also providing the high rate discharge capabilities required for defibrillators and ICDs. The manufacturer can rely on a lithium-ion battery having no voltage delay properties of its own, and comparatively stable internal resistance and charge state, to supply the defibrillation energy rapidly and consistently.

An additional benefit of this use of a lithium-ion secondary battery in conjunction with a voltage boost/charge control circuit is the higher source voltage available to the defibrillator inverter circuitry that charges the energy storage capacitors. The higher source voltage mitigates the effects of circuit current/resistance losses in the inverter that become more significant as the source voltage decreases. The lithium-ion battery voltage is typically 3.5 to 4.0 volts as opposed to 2.0 to 3.0 volts for a Li/SVO cell of the type presently used in implantable defibrillators and ICDs. Also, the lithium-ion cell provides a significant advantage over other lithium chemistries such as $LiV_2O_5$ at 2.8 volts and $LiTiS_2$ at 2.2 volts, which are identified as candidate secondary batteries in U.S. Pat. No. 5,674,248 of Kroll et al., discussed by way of background above.

Illustrated Embodiments

Figure 1:
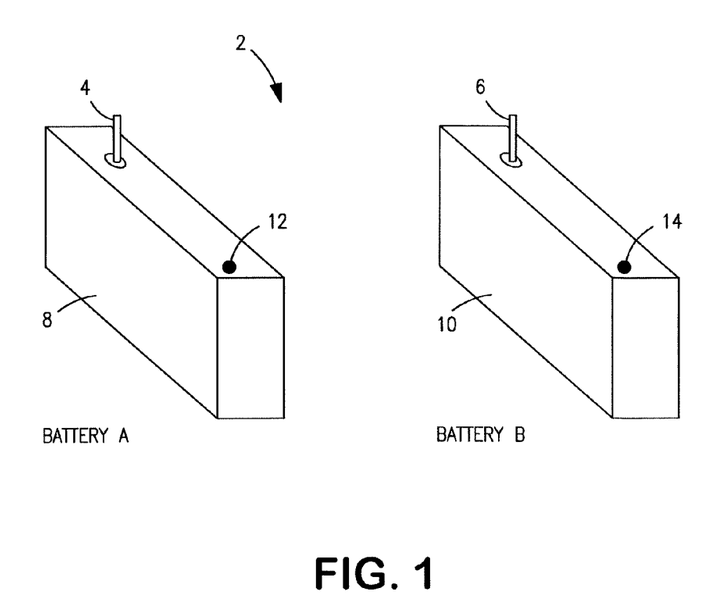
FIG. 1 is a diagrammatic perspective view showing primary and secondary batteries in accordance with the invention.

Referring now to the Drawings in detail wherein like reference numerals have been used throughout the various figures to designate like elements, there is shown in FIG. 1 an illustration of two segments of a hybrid battery power source 2, namely, a primary battery "A" and a secondary battery "B". By way of example only, the primary battery "A" will be assumed to incorporate either a Li/CFx, $Li/BrCl_2$, $Li/MnO_2$, $Li/SO_2Cl_2$, $Li/SOCl_2$ or Li/SVO battery chemistry, and the secondary battery "B" will be assumed to incorporate a rechargeable lithium-ion chemistry. Such batteries are standard commercial products that are available from Wilson Greatbatch Technologies, Inc. of Clarence, N.Y. as catalog items. FIG. 1 also depicts that for each of battery "A" and battery "B", one electrical connection can be made via the vertical pins 4 and 6 respectively protruding from the top of cases 8 and 10. The pins 4 and 6 represent the positive (cathode) terminals of the batteries. A second electrical connection can be made to the cases 8 and 10 themselves, and case contacts 12 and 14 are respectively shown. These case contacts represent the negative (anode) terminals of the batteries.

Figure 2:
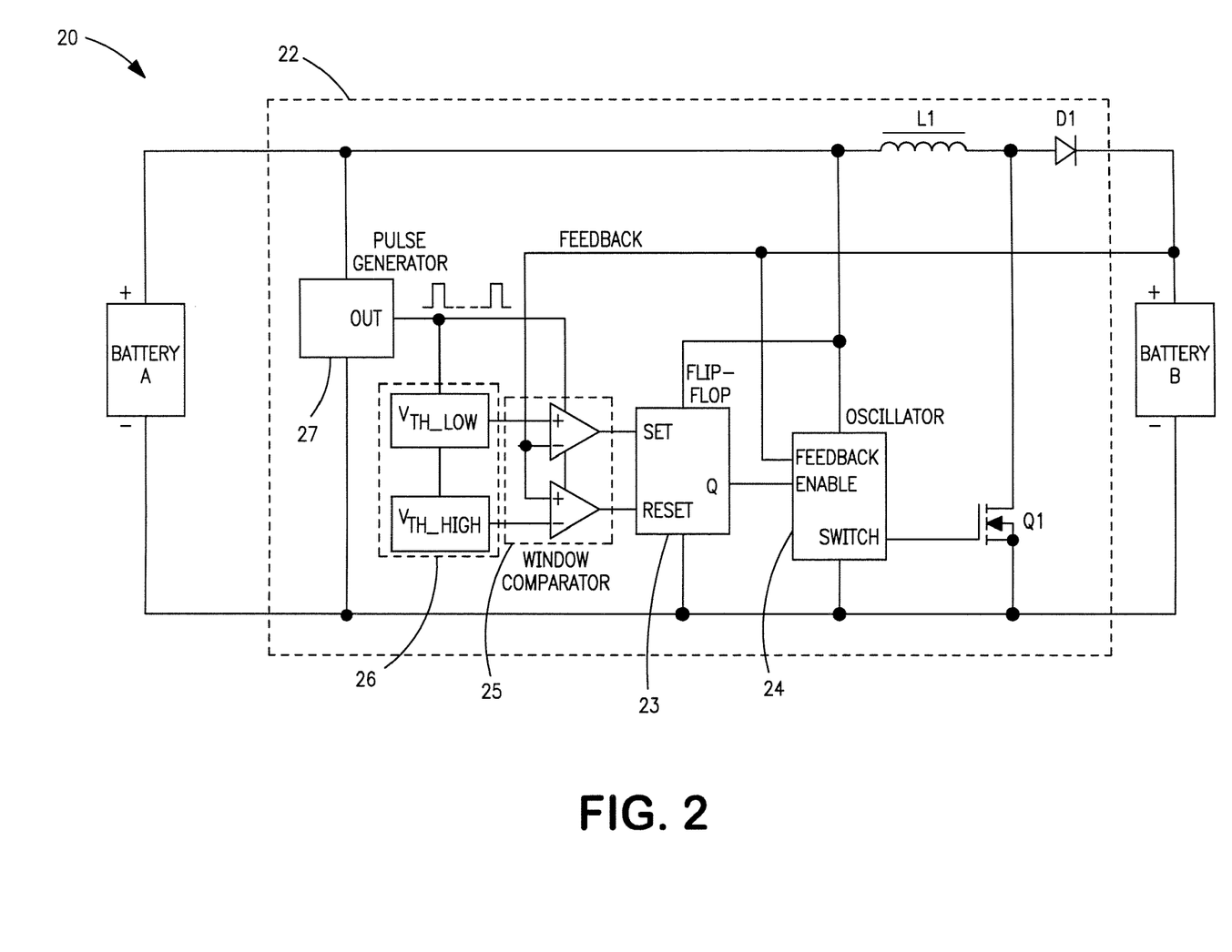
FIG. 2 is a schematic diagram showing an exemplary hybrid battery power source comprising a primary segment battery "A" and a secondary segment battery "B" connected by a voltage boost/charge control circuit having an inductor and a pulse generating control circuit therein.

Turning now to FIG. 2, an exemplary hybrid battery power source 20 is shown. This power source includes the primary battery "A" and the secondary battery "B" of FIG. 1. Battery "A" and battery "B" are connected in parallel with a switching-type voltage boost/charge control circuit 22 interposed between the two batteries to charge the secondary battery "B" to a higher potential than the primary battery "A" and to regulate the applied charging current and maximum cell charge/discharge voltage excursions. By way of example, a 2.8-volt Li/CFx or 3.5 volt $Li/BrCl_2$ or 3.0 volt $Li/MnO_2$ or 3.5 volt $Li/SO_2Cl_2$ or 3.5 volt $LiS/OCl_2$ or 2.6-volt Li/SVO primary battery "A" will have its voltage boosted to about 3.8 to 4.0 volts for recharging a lithium-ion secondary battery "B." Within the circuit 22 is a conventional oscillator-type pulse control circuit 24 that provides variable width/duty cycle charging pulses to charge the secondary battery "B" to a relatively constant potential even though the voltage level of the primary battery "A" may vary through some range. By way of example, if the primary battery "A" is an Li/SVO or Li/CFx battery and the secondary battery "B" is a lithium-ion battery, the charging voltage on the secondary battery "B" can be maintained at a fairly constant level of 3.5 to 4.0 volts even though the output of the primary battery "A" varies between about 2.0 to 3.0 volts during its service life. Thus, within the life of the primary battery "A," every defibrillator charging cycle will occur at nearly the same rate due to the regulated charge state and, hence, constant voltage output of the secondary battery "B."

In FIG. 2, the primary battery "A" delivers energy to the input of the circuit 22 while the output of the circuit 22 is connected to the secondary battery "B." The basic principle of operation for the circuit 22 is as follows:

The control circuit 24 derives prime power from the primary battery "A" and includes an oscillator function. The control circuit's output labeled "Switch" is toggled rapidly (e.g. 100 kHz) to turn the field effect transistor Q1 on and off.

Each time that transistor Q1 is turned on, current flow increases in the inductor L1 and energy is imparted to the magnetic field associated with the inductor. A rectifier diode D1 is reverse biased and prevents current flow from the secondary battery "B" backward in to Q1.

When transistor Q1 is turned off, the magnetic field collapses in the inductor L1 and returns the energy to the circuit, causing the voltage across the inductor to increase.

The collapsing magnetic field in the inductor develops a higher positive voltage at the anode of rectifier diode D1. The diode D1 becomes forward biased and current flows from the inductor L1 through the diode and into the secondary battery "B," transferring energy to that battery.

The circuit labeled "Feedback" samples the voltage at the secondary battery "B" and controls the rate of switching of transistor Q1 to regulate the flow of energy to battery "B" and, hence, the charge imparted to that battery.

This feedback voltage is also applied to a conventional window voltage comparator 25 which compares the battery "B" voltage against two predetermined reference voltages "Vth_low" and "Vth_high" 26 which, by way of example, might be 3.7 and 3.9 volts respectively. When the terminal voltage of battery "B" falls below "Vth_low" the first comparator output is asserted. This output is connected to the "Set" input of Flip-Flop 23 so that the Flip-Flop is toggled to the set state.

Similarly, when the terminal voltage of battery "B" rises above "Vth_high" the second comparator output is asserted. This output is connected to the "Reset" input of flip-flop 23 so that the flip-flop is toggled to the reset state. This configuration results in flip-flop 23 being toggled to the "set" state when the battery "B" voltage falls below a first predetermined value and being toggled to the "reset" state when the battery "B" voltage rises above a second predetermined value.

The output "Q" of flip-flop 23 is connected to the "Enable" input of the control circuit 24. This function provides the control required via the circuit labeled "Enable" to enable the control circuit 24 only if the battery "B" voltage falls below a minimum value and to continue to charge battery "B" only until its terminal voltage has risen to a maximum acceptable value. At that point the "Enable" signal will be negated to prevent overcharging of battery "B".

The flip-flop 23 is implemented with metal oxide semiconductor field effect transistors (MOSFETs) or similar devices which require little or no bias current to effect device switching in order to reduce quiescent current drain to an absolute minimum.

An additional benefit of this circuit not previously disclosed is provided by the pulse generator 27. The charge control circuitry must derive prime power from one of the two batteries, in this case battery "A". In order to minimize the current drain on battery "A" needed to support the circuitry, the voltage reference 26 and window comparator 25 are powered by the output of the pulse generator 27. The pulse generator 27 is similar to oscillator circuits well known in the pacemaker industry, whereby energy is slowly extracted from a battery and used to charge a capacitor. The capacitor is then rapidly discharged to deliver a higher amount of power in a shorter period of time. In this embodiment the pulse generator 27 output is used to power the voltage reference 26 and window comparator 25 circuitry so that the circuitry is only energized periodically, e.g. once per minute.

By intermittently energizing the voltage reference 26 and window comparator 25 and controlling the state of the control circuit 24 with a low power flip-flop 23, this embodiment significantly reduces the quiescent current drain on the battery and therefore provides a significant improvement in service life.

As indicated, the primary benefit of the hybrid battery power source 20 of FIG. 2 is that the secondary battery "B" can be charged and maintained at a higher working voltage than the primary battery "A," and virtually all of the capacitor charging energy can be derived from the secondary battery. By using voltage boosting and control circuitry having an inductive component connected between the primary and secondary batteries, increased voltage is delivered to the secondary battery "B" for recharging it to above the voltage of the primary battery "A." Moreover, the charging current is controlled by means of a variable pulse width and/or duty cycle control, allowing it to operate over a range of voltages on the primary battery "A," such as about 2.0 volts to 3.0 volts for an Li/SVO or Li/CFx battery, in all cases charging the secondary battery "B" to a higher voltage, such as 3.5 to 4.0 volts for a lithium-ion battery. Thus, throughout the life cycle of the primary battery "A," the secondary battery "B" will be delivering the same voltage to charge the capacitors in the defibrillator or ICD. This represents a significant advantage over prior art power sources, both in the short charge time and in the constancy of the charge going to the secondary battery "B." The full charge capacity of the primary battery "A" is thus available. The pulse width and/or duty cycle of the pulse control circuit 24 is simply varied to maintain a constant charging voltage on the secondary battery "B" regardless of where the primary battery "A" is in its life cycle. Note that for a lithium-ion secondary battery "B" charged to 4.0 volts and operating at a current of 3.0 amperes with a conversion efficiency of 67 percent, a five second charge time is all that would be required to develop a 40 joule pulse. Again, this minimal charge time is a distinct improvement over previous defibrillator batteries.

Another benefit of the hybrid battery power source 20 that has not been previously disclosed in the prior art is the capability to regulate the flow of recharge energy from the primary battery "A" to the secondary battery "B." Regulation of the rechargeable battery charge state is a necessity for optimum energy storage because of the effects of irreversible discharge capacity fade and increased cell internal resistance as a lithium-ion rechargeable cell is cycled. In particular, as reported by Spotnitz, R., "Simulation of Capacity Fade in Lithium-ion Batteries", *Journal of Power Sources,* 113, 72–80, (2003), the maximum SOC applied to a lithium-ion cell as well as the depth of discharge affects capacity fade and internal resistance. In conventional rechargeable battery applications where the batteries may be readily replaced, the practice is to maximize the charge and depth of discharge in order to obtain maximum output capacity from the battery. However, in high energy medical device applications, applicants have determined that limiting maximum SOC and depth of discharge are necessary in order to ensure optimal pulse delivery characteristics. For a lithium-ion cell, charging to a maximum SOC of 3.9 V and attempting to limit the depth of discharge to 0.2 V (3.7 V minimum SOC) should provide adequate energy output while minimizing capacity fade and internal resistance increase over time. Additional data on the relationship between SOC and internal resistance for lithium-ion batteries has been reported by Wright, R. B. et. al. in "Calendar- and cycle-life studies of advanced technology development program generation I lithium-ion batteries", *Journal of power Sources,* 110, 445–470, (2002).

Figure 3A:
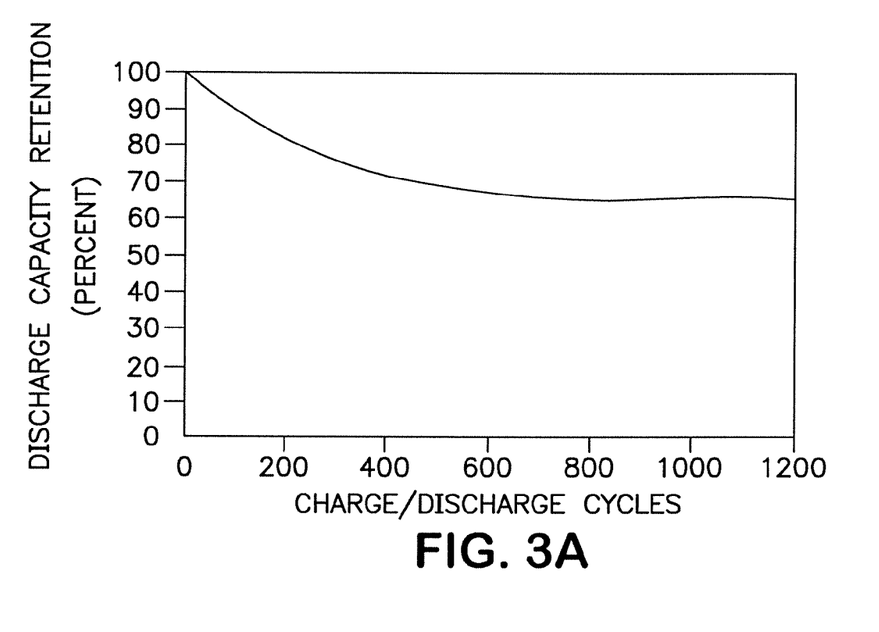
FIG. 3A is a graph which shows the relationship between energy capacity and the number of charge/discharge cycles for a typical lithium-ion cell.

Referring now to FIG. 3A, a graph is shown of the discharge capacity retention versus the number of charge/discharge cycles for a representative lithium-ion battery. When first placed into service the battery provides a maximum energy storage capacity that diminishes as the battery is subjected to charging and discharging cycles. Reduced discharge capacity in the secondary battery will manifest itself as a reduction in the number of defibrillator charges that may be delivered before the secondary battery requires charging. This degradation in discharge capacity is a strong function of the maximum SOC and depth of discharge that the battery is subjected to in each cycle. This degradation can be minimized by configuring the voltage boost/charging control circuit 20 to limit the charge/discharge excursions during the device life.

Figure 3B:
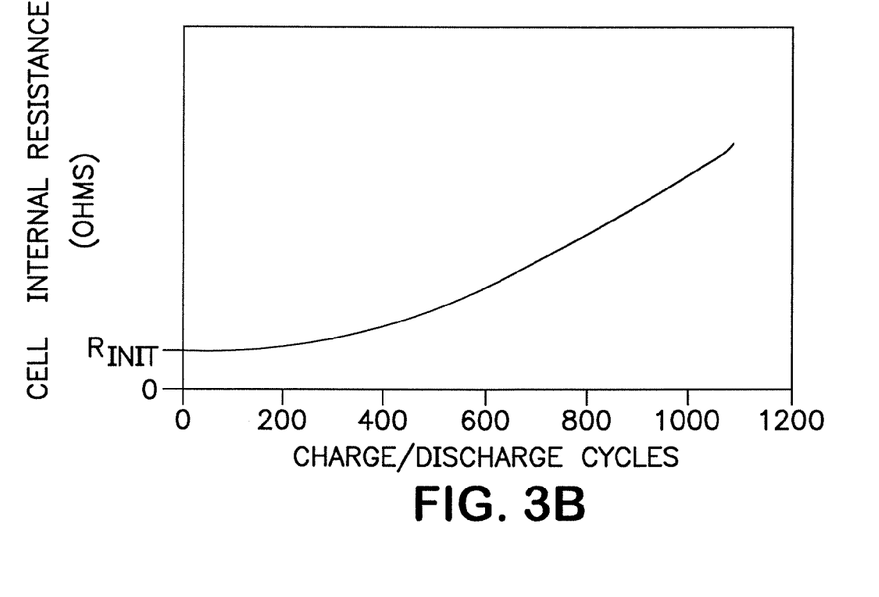
FIG. 3B is a graph which shows the relationship between cell internal resistance and the number of charge/discharge cycles for a typical lithium-ion cell.

Referring now to FIG. 3B, a graph is shown of the cell internal resistance versus the number of charge discharge cycles for a representative lithium-ion battery. When first placed into service the battery exhibits minimum internal resistance that increases as the battery is subjected to charging and discharging cycles. Increased cell internal resistance in the secondary battery will manifest itself as an increase in the time required to fully charge the defibrillator energy storage capacitors because of the diminished ability to deliver high discharge currents. This increase in cell internal resistance is again a strong function of the maximum SOC and depth of discharge that the battery is subjected to in each cycle. This degradation can therefore be minimized by configuring the voltage boost/charging control circuit 20 to limit the charge/discharge excursions during the device life.

Figure 4:
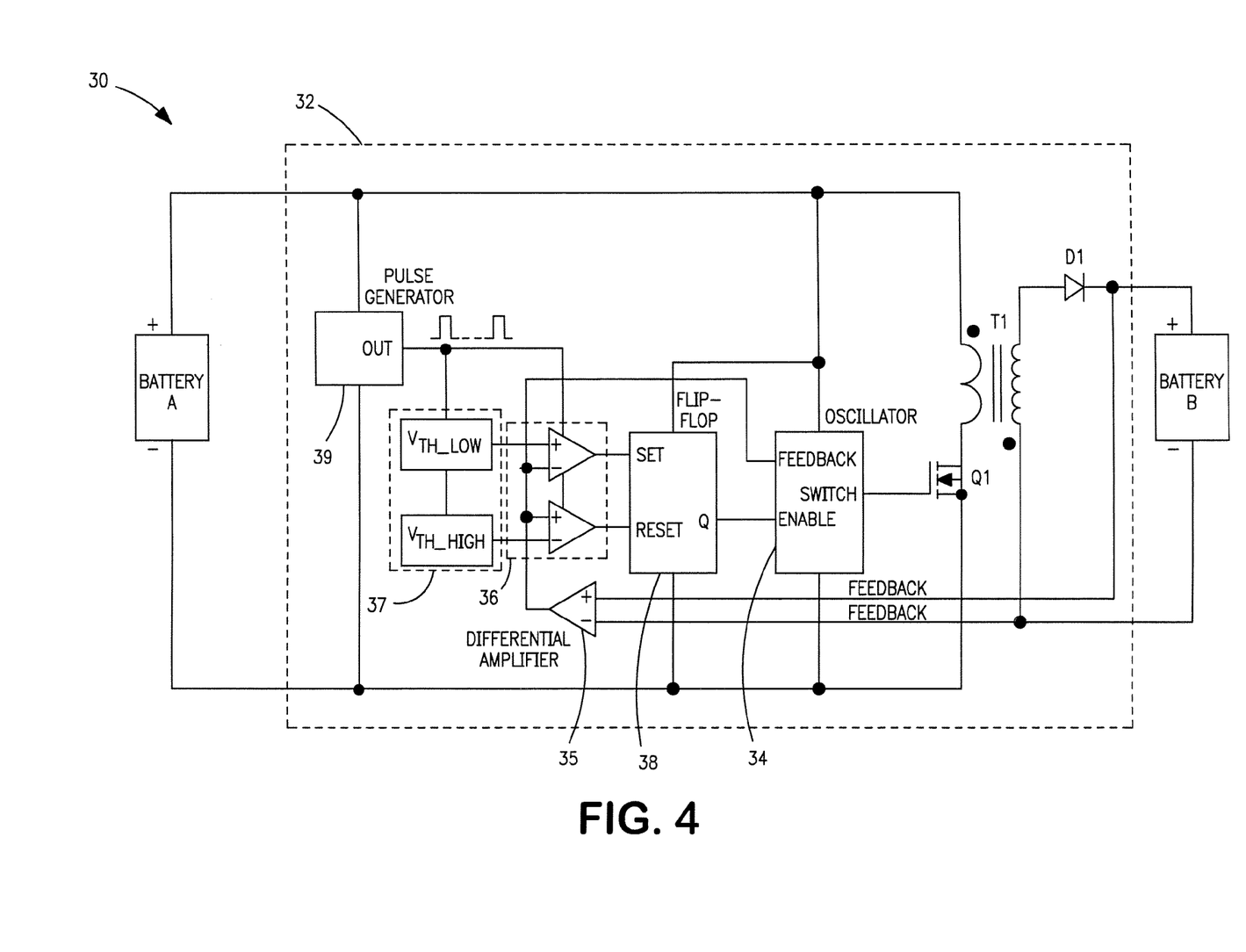
FIG. 4 is a schematic diagram showing another exemplary hybrid battery power source comprising a primary segment battery "A" and a secondary segment battery "B" connected by another voltage boost/charge control circuit having a flyback transformer and a pulse generating control circuit therein.

Turning now to FIG. 4, another exemplary hybrid battery power source is shown. This power source includes the primary battery "A" and the secondary battery "B" of FIG. 1. Battery "A" and battery "B" are connected in parallel with a voltage boost/charge control circuit 32 containing a conventional oscillator-type pulse control circuit 34, but with the voltage boost function being implemented with a flyback converter. In particular, instead of utilizing a series inductor to boost the charging voltage to battery "B," a transformer T1 with primary and secondary connections is used. Although this represents a minor complication in circuitry, it permits complete isolation of the circuits connected to the primary and secondary sides of the transformer. In FIG. 4, the primary battery "A" again provides the prime power for the circuit, and its output is connected to the input of the circuit 32. The pulse output of the circuit 32 charges the secondary battery "B." The basic principles of operation for the circuit 32 are as follows:

The control circuit 34 derives prime power from the primary battery "A" and again includes an oscillator function. The control circuit's output labeled "Switch" is toggled rapidly (e.g. 100 kHz) to turn the field effect transistor Q1 on and off.

Each time that transistor Q1 is turned on, the current in the primary winding of transformer T1 increases and energy is stored in the magnetic field associated with the transformer. The connection of the secondary winding is reversed in the sense that the induced voltage at the anode of rectifier diode D1 is negative such that the rectifier is reverse biased and no current flows in the secondary winding while the magnetic field is increasing. The number of turns for the secondary winding may be larger than that of the primary in order to provide a voltage boost function.

When the control circuit 34 turns off transistor Q1 the magnetic field begins to collapse, causing voltages of opposite polarity to be induced across both the primary and secondary windings. Because these voltages are opposite in polarity, the anode of diode D1 is driven to a positive polarity, causing this rectifier to conduct and current to flow, thereby delivering energy to secondary battery "B."

The circuits labeled "Feedback" sample the voltage of the secondary battery "B". This feedback voltage is applied to a differential amplifier 35 whose output is provided to a conventional window voltage comparator 36. The differential amplifier 35 senses the terminal voltage of battery "B" while maintaining electrical isolation between the negative circuits of batteries "A" and "B". The voltage output of differential amplifier 35 is representative of the terminal voltage of battery "B" regardless of any voltage difference between the battery "A" and battery "B" negative circuits.

The output of differential amplifier 35 is also applied to the Feedback input of the control circuit 34 to vary the rate of switching of transistor Q1. This provides the means to regulate the flow of energy to the secondary battery "B" and, hence, the charge imparted to that battery.

Window voltage comparator 36 compares the battery "B" voltage against two predetermined reference voltages "Vth_low" and "Vth_high" which, by way of example, might be 3.7 and 3.9 volts respectively. When the terminal voltage of battery "B" falls below "Vth_low" the first comparator output is asserted. This output is connected to the "Set" input of flip-flop 38 so that the flip-flop is toggled to the "set" state.

Similarly, when the terminal voltage of battery "B" rises above "Vth_high" the second comparator output is asserted. This output is connected to the "Reset" input of flip-flop 38 so that the flip-flop is toggled to the "reset" state. This configuration results in flip-flop 38 being toggled to the "set" state when the battery "B" voltage falls below a first predetermined value and being toggled to the "reset" state when the battery "B"

voltage rises above a second predetermined value. This function provides the control required to enable the pulse control circuit 34 only if the battery "B" voltage falls below a minimum value and to continue to charge battery "B" only until its terminal voltage has risen to a maximum acceptable value. At that point the "Enable" signal will be negated to prevent overcharging of battery "B".

The flip-flop 38 is implemented with metal oxide semiconductor field effect transistors (MOSFETs) or similar devices which require little or no bias current to effect device switching in order to reduce quiescent current drain to an absolute minimum.

An additional benefit of this circuit not previously disclosed is provided by the pulse generator 39. The charge control circuitry must derive prime power from one of the two batteries, in this case battery "A". In order to minimize the current drain on battery "A" needed to support the circuitry, the voltage reference 37 and window comparator 36 are powered by the output of the pulse generator 39. The pulse generator 39 is similar to oscillator circuits well known in the pacemaker industry, whereby energy is slowly extracted from a battery and used to charge a capacitor. The capacitor is then rapidly discharged to deliver a higher amount of power in a shorter period of time. In this embodiment the pulse generator 39 output is used to power the voltage reference 37 and window comparator 36 circuitry so that the circuitry is only energized periodically, e.g. once per minute.

By intermittently energizing the voltage reference 37 and window comparator 36 and controlling the state of the control circuit 34 with a low power flip-flop 38, this embodiment significantly reduces the quiescent current drain on the battery and therefore provides a significant improvement in service life.

The primary benefit of the hybrid battery power source 30 of FIG. 4 relative to the FIG. 2 design is that the primary and secondary batteries "A" and "B" do not share a common return circuit.

The voltage boost/charge regulator circuits described in the embodiments of FIGS. 2 and 4 are capable of providing charging currents for the secondary battery "B" in the range of milliamperes to hundreds of milliamperes. This characteristic provides for rapid recharging of the secondary battery but also requires the primary battery "A" to supply significant discharge current. Primary battery chemistries such as Li/CFx and Li/MnO$_2$ are capable of supporting these discharge rates but Li/I batteries cannot support discharge currents above 100 microamperes because of their inherently high internal resistance. In some cases, it may be desirable to use a Li/I chemistry for the primary battery "A" of an implantable defibrillator or ICD insofar as such batteries are already commonly used for implantable pacemakers and are commonly available.

Figure 5:
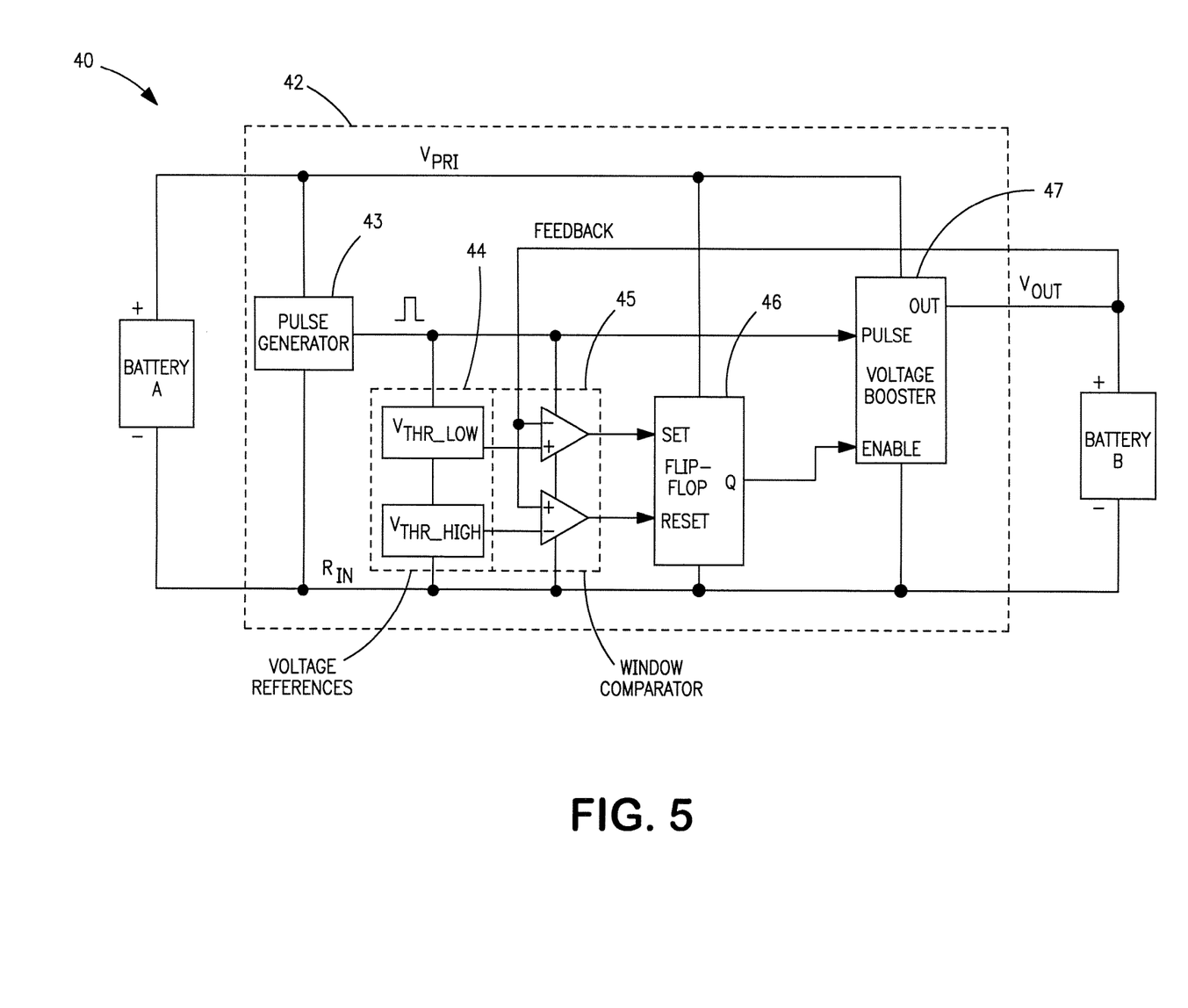
FIG. 5 is a schematic diagram showing another exemplary hybrid battery power source comprising a primary segment battery "A" and a secondary segment battery "B" connected by another voltage boost/charge control circuit having a non-inductive pulse-driven voltage booster and a pulse generating control circuit therein.

Turning now to FIG. 5, another exemplary hybrid battery power source 40 is shown that will allow the use of a Li/I primary battery. The power source 40 includes a primary battery "A" and a secondary battery "B" as in FIG. 1. Battery "A" and battery "B" are connected in parallel with a voltage boost/charge control circuit 42. In the embodiment of FIG. 5, the charging current for the secondary battery "B" can be applied using pulses that are shorter in duration than is practical for the embodiments of FIGS. 2 and 4. This reduces the charging rate for the secondary battery "B" but also reduces the discharge rate of the primary battery "A" to a level that is compatible with Li/I primary cells. The embodiment of FIG. 5 would thus be entirely suitable for an application where it is not necessary to recharge the secondary battery "B" in a period of less than two to five days.

As was the case with the embodiments of FIGS. 2 and 4, the voltage boost/charge control circuit 42 is powered by primary battery "A" and provides a higher output voltage for the purpose of charging secondary battery "B." The circuitry also monitors the voltage of secondary battery "B" to control the charging current in order to maintain the secondary battery within the desired range of state of charge. The operation of this circuitry is as follows:

A pulse generator circuit 43 is powered by primary battery "A" to produce a periodic output voltage pulse with a duration of one millisecond and a repetition period of one to two seconds. This circuitry is exemplified by pulse generators utilized in implantable pacemakers.

The voltage output pulse is provided as prime power to the voltage references 44 and window comparator 45 such that they are operational only for the duration of the voltage pulse. This intermittent operation serves to significantly reduce the power consumption of the circuitry.

The voltage references 44 provide two stable reference voltages, e.g. Vthr_low=3.6 volts and Vthr_high=3.9 volts.

The voltage of secondary battery "B" is provided as an input to the window comparator 45 in order to affect the operation of the circuitry based upon the state of charge of the secondary battery. This feedback voltage is compared to the two stable reference voltages so that one comparator output changes state when the feedback voltage falls below the lower reference voltage and the second comparator output changes state when the feedback voltage rises above the higher reference voltage.

The two outputs of the window comparator 45 are connected to the "Set" and "Reset" inputs of flip-flop 46 such that the flip-flop is toggled to the "SET" state when the secondary battery "B" voltage falls below the lower reference voltage and, conversely, the flip-flop is toggled to the "RESET" state when the secondary battery "B" voltage rises above the higher reference voltage.

The output "Q" of the flip-flop 46 is connected to the "Enable" input of a voltage booster circuit 47 so that the voltage booster is operational only when the flip-flop 46 is in the "SET" state. In this configuration the voltage booster 47 will be operational only after the secondary battery "B" voltage has fallen below the lower reference voltage and only until the secondary battery "B" voltage rises above the higher reference voltage.

The voltage booster circuit 47 is triggered by the pulse generator 43 so that the voltage booster circuit produces output voltage pulses to transfer energy to the secondary battery "B".

Figure 6:
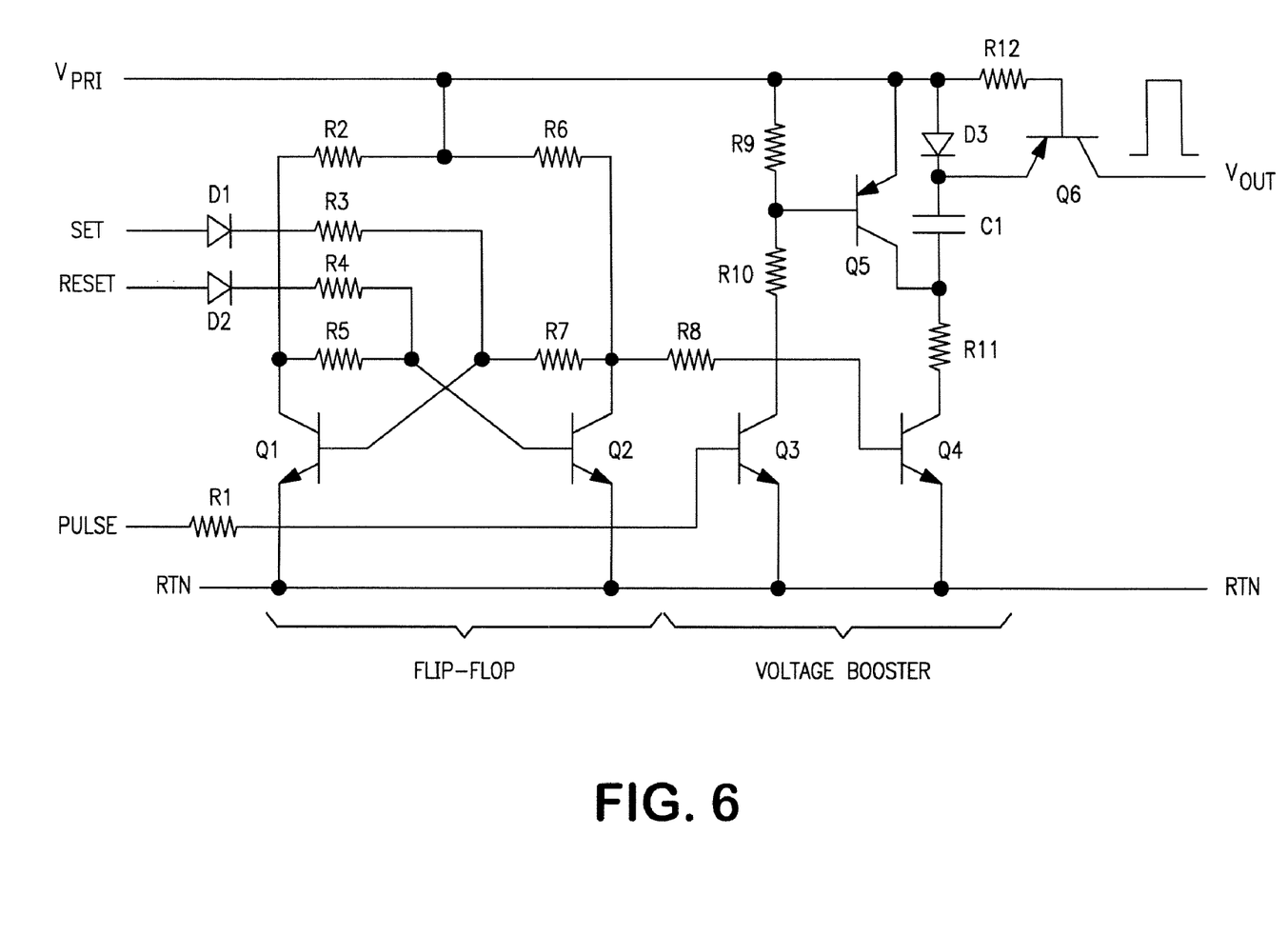
FIG. 6 is a schematic diagram showing additional details the voltage booster shown in FIG. 5, along with a charge controlling flip-flop.

Referring now to FIG. 6, the operation of the flip-flop 46 and voltage booster 47 is described in additional detail, as follows:

When flip-flop 46 is in the "RESET" state, transistor Q2 is biased on, resulting in the flow of collector current and a low voltage on Q2 collector due to voltage drop across resistor R6. No current flows in resistor R7 to bias transistor Q1, so the collector voltage of Q1 is high, allowing current flow through resistor R5 so that transistor Q2 remains biased on. The "SET" input is negated so that its voltage is approximately equal to the "RTN" return voltage.

If the "SET" input is momentarily asserted by raising the applied voltage, diode D1 will be forward biased and conduct, causing the base voltage of Q1 to rise and collector current to flow through resistor R2. When Q1 is no longer biased off the collector voltage will fall due to voltage drop through resistor R2 and no current will flow through resistor R5, eliminating the bias current for Q2. Q2 will cease to conduct collector current, allowing the collector voltage to rise and supply bias current for Q1 through resistor R7.

Conversely, if Q2 is biased off and the "RESET" input is momentarily asserted by raising the applied voltage, the base-emitter junction of transistor Q2 will be forward biased and Q2 will conduct collector current. This current will cause a voltage drop in resistor R6 so that the collector voltage of Q2 falls, causing Q1 to be biased off because bias current no longer flows through resistor R7. With Q1 biased off the collector voltage rises and allows bias current for Q2 to flow through resistor R5. The flip-flop will therefore remain in either the "SET" or "RESET" state indefinitely until a trigger pulse is applied to the converse input.

While flip-flop 46 is in the "SET" state current will flow through resistor R8 to the base of transistor Q4 so that Q4 is biased on. Current will flow through the collector of Q4 and through D3, C1 and R11 so that a charge accumulates on capacitor C1.

Each time that a positive voltage pulse is applied to the "PULSE" input of the circuit, the base-emitter junction of Q3 will be forward biased and Q3 will conduct current through its collector terminal. This current will be supplied by resistors R9 and R10.

When current flows through R9 and R10 the voltage drop across R9 will cause the base-emitter junction of Q5 to be forward-biased so that Q5 will be biased on. This will lift the collector voltage to a value approximately 0.3 volts less than the emitter voltage.

Capacitor C1 will be charged to the full supply voltage Vpri between the voltage pulses applied to the "PULSE" input. Each time that the "PULSE" input is asserted and transistor Q5 is biased on, the lower potential end of C1 will be pulled up by the collector of Q5. The higher potential end of C1 will rise to almost twice the supply voltage Vpri.

When the higher potential end of C1 rises above Vpri diode D3 will be reversed biased and the base-emitter junction of transistor Q6 will be forward biased so that energy stored in C1 will flow through Q6 to battery "B."

When the "PULSE" input is negated, transistors Q3 and Q5 will be biased off and C1 will be recharged through Q4, D3 and R11.

The circuit of FIGS. 5 and 6 thus provides a pulsed output voltage that is nearly twice the amplitude of the supply voltage under the control of the voltage references 44 and window comparator 45.

Figure 7:
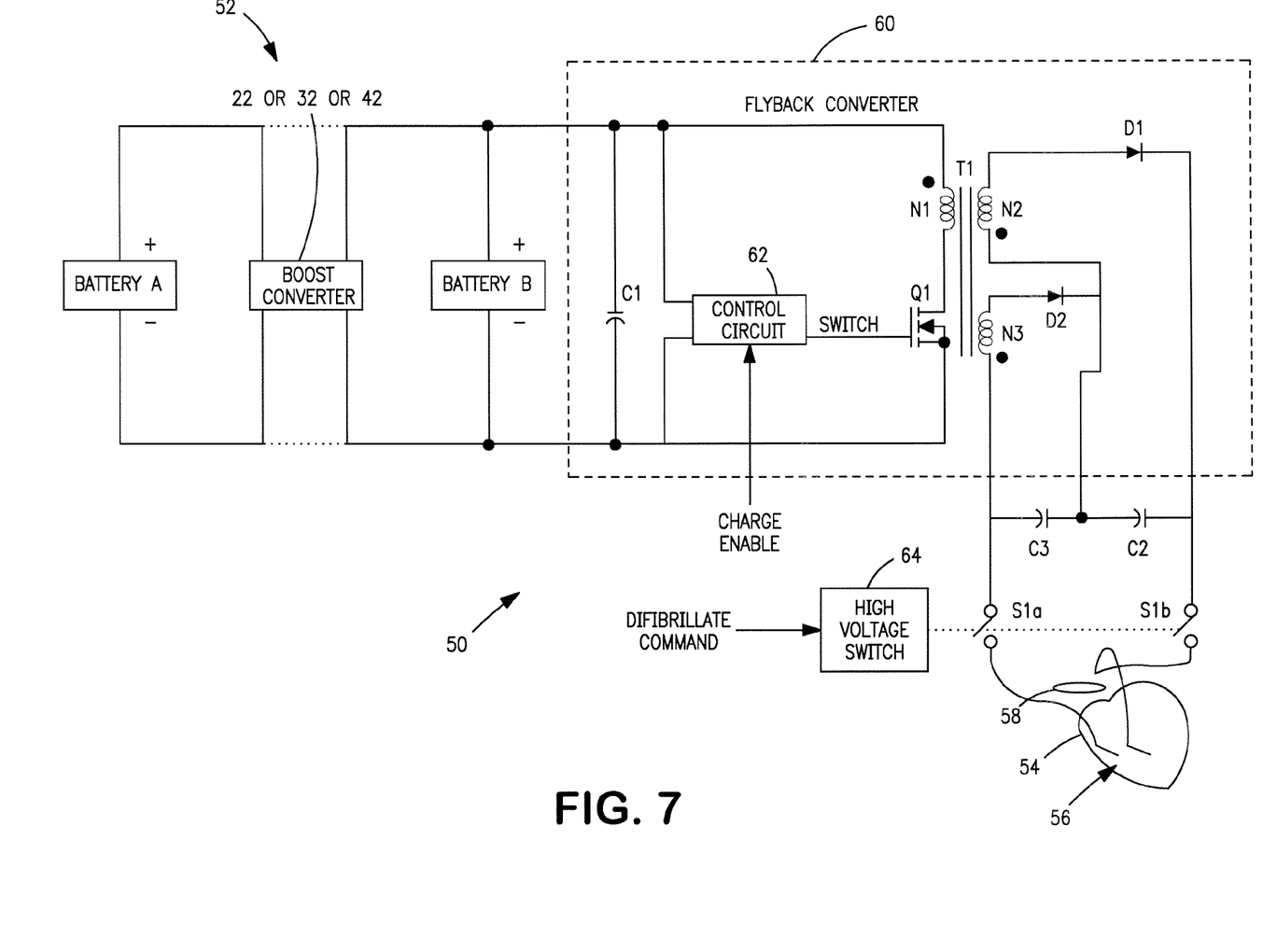
FIG. 7 is a schematic diagram showing a hybrid battery power source of the invention arranged in a defibrillator and discharging into a voltage amplification system.

Turning now to FIG. 7, a battery powered high energy medical device is embodied as a defibrillation system 50 that is shown schematically to include a hybrid battery power source 52 and other circuits and devices for defibrillating a heart 5 using high voltage pulses. The hybrid battery power source 52 includes the primary and secondary batteries "A" and "B" described above. Batteries "A" and "B" are preferably connected in parallel via one of the voltage boost/charge control circuits 22 or 32 or 42 as described above relative to FIGS. 2, 4, 5 and 6. The defibrillation system 50 includes physiologic electrodes 56 that are attached to cardiac tissue of the heart 54 for the purposes of monitoring cardiac activity and delivering electrical energy in the event that cardiac activity becomes abnormal. The electrodes are connected to the defibrillation system 50 via conventional leads 58. A conventional voltage amplification system or flyback converter circuit 60 having an oscillator-type control circuit 62 therein is also provided as part of the defibrillator system 50. A description of defibrillation operation for the depicted subsystems follows:

Circuitry (not shown) that is part of the defibrillation system 50 will monitor the activity of the cardiac muscle. Should the monitored cardiac activity indicate the need for delivery of a defibrillation charge, the signal labeled "Charge Enable" will be asserted to activate the control circuit 62 that is part of the flyback converter circuit 60. This will begin a capacitor charge sequence for charging energy storage capacitors C2 and C3.

The control circuit 62 derives prime power from the batteries "A" and "B" and includes an oscillator function. Capacitor C1 provides high frequency decoupling of, and lowers the AC source impedance for, the hybrid battery power source 52 to the flyback converter 60. As stated, the hybrid battery power source 52 can be constructed in accordance with any of the embodiments of FIGS. 2, 4, 5–6 or modifications thereof. The control circuit output labeled "Switch" is toggled rapidly (e.g. 100 kHz) to turn transistor Q1 on and off.

Each time that the transistor is turned on, the current in the primary winding of transformer T1 increases and energy is stored in the magnetic field associated with the transformer. The connection of the secondary windings is reversed in the sense that the induced voltages at the anodes of rectifier diodes D1 and D2 is negative such that the diodes are reverse biased and no current flows in the secondary windings while the magnetic field is increasing.

When the control circuit 62 turns off transistor Q1 the magnetic field begins to collapse, causing voltages of opposite polarity to be induced across both the primary and secondary windings. Because these voltages are opposite in polarity, the anodes of diodes D1 and D2 are driven to a positive polarity, causing the diodes to conduct and current to flow, delivering energy to energy storage capacitors C2 and C3.

The number of turns in the secondary windings is much larger than that of the primary, by a ratio of perhaps 100 to 1, in order to achieve a large voltage boost function. Because of the large turns ratio, the low primary winding voltage will be increased to a high secondary winding voltage, the multiplication factor being nearly equal to the turns ratio. In this manner, a four volt prime power source may be increased to hundreds of volts.

Two galvanically isolated secondary windings on transformer T1 have an identical number of turns and are each connected to energy storage capacitors C2 and C3. This connection causes the capacitors to be simultaneously charged in a parallel manner.

At the completion of the charge cycle, the defibrillation system control circuitry negates the signal labeled "Charge Enable" and asserts the signal labeled "Defibrillate Command." This signal activates the high voltage switch 64 depicted as two switch circuits S1a and S1b. These switch circuits connect the energy storage capacitors C2 and C3 in a series configuration to the wires leading to the physiologic electrodes attached to the cardiac tissue. The energy stored in the capacitors C2 and C3 is rapidly delivered to the heart to provide the therapeutic benefit.

The defibrillator system of FIG. 7 thus utilizes a flyback converter 60 that has primary and secondary transformer windings in the circuit providing isolation from the hybrid battery power source 52. This allows a modification in which multiple transformers can be used, with the primary sides thereof being connected in series or parallel and the secondary sides thereof likewise being connected in series or parallel. This would provide voltage multiplication in case it is desired to multiple capacitor banks.

Rationale for Configuration

The configuration of batteries and circuitry described above in connection with the various drawing figures, provides an improvement in the performance of implantable defibrillators and ICDs by reducing charge times to manageable and predictable levels. These configurations provide the additional benefit of utilizing the stored energy of the primary battery to maximum extent, thereby increasing the service life for the defibrillator system. As previously described herein, a fundamental requirement for the power source in an implantable defibrillator/ICD application is the ability to deliver a large amount of energy to the circuitry rapidly in order to charge the energy storage capacitors in the shortest time possible. A second requirement of nearly equal importance is the maximum utilization of stored energy within the power source in order to provide maximum service life for the implanted device.

The rate at which power can be delivered from a battery or other electrical energy source to a load is inversely proportional to the internal resistance or impedance of the energy source. This is due to the fact that the load current flows through the internal resistance of the battery and the resulting power is dissipated as waste heat within the battery structure. In order to reduce the time required to charge the energy storage capacitors, the charging circuit must draw higher load current from the battery. All of the primary battery chemistries discussed above produce an internal resistance that renders them less able to supply high peak currents as well as the lithium-ion battery. This can be seen in Table 1 below.

TABLE 1

| Battery Chemistry | Voltage Range (VDC) | Internal Resistance (ohms) | Energy Density (Wh/cm$^3$) |
|---|---|---|---|
| Lithium - CFx (primary) | 2.8–2.0 | 5–10 | 0.8–0.9 |
| Lithium - BrCl$_2$ (primary) | 3.5–3.0 | 20–30 | 0.8 |
| Lithium - MnO$_2$ (primary) | 3.0–2.5 | 15–20 | 0.6 |
| Lithium - SO$_2$Cl$_2$ (primary) | 3.5–3.0 | 10–20 | 0.8 |
| Lithium - SOCl$_2$ (primary) | 3.5–3.3 | 10–20 | 0.8 |
| Lithium - SVO (primary) | 3.0–2.0 | 0.5–1.0 | 0.4 |
| Lithium - Ion (rechargeable) | 4.0–3.5 | 0.1–0.5 | 0.2 |

The internal resistance values given above are average values. It will be seen that the internal resistances of the Li/CFx, Li/BrCl$_2$, Li/MnO$_2$, Li/SO$_2$Cl$_2$ and Li/SOCl$_2$ battery chemistries are the highest among the primary batteries, and this internal resistance renders such batteries unsuitable for defibrillators and ICDs if used alone. The internal resistance of the Li/SVO battery chemistry is substantially lower than that of the other primary batteries. As noted above, however, the internal resistance of Li/SVO batteries can increase to unacceptable levels during battery run-down. These batteries are thus susceptible to voltage delay effects, it may be concluded that they are somewhat unreliable for implantable defibrillator and ICDs if used alone.

By comparison, the internal resistance of the lithium-ion rechargeable battery is low and relatively stable. However, it will be seen that its energy density is also substantially lower than that of the primary batteries. In regard to battery energy density and device service life, it is known that for a given battery volume, the highest energy density battery will possess the largest total energy and will, logically, provide the longest device service life. If the primary batteries are compared based upon energy density, the data in Table 1 indicate that the Li/CFx battery chemistry should provide the longest device service life, with the Li/BrCl$_2$, Li/SO$_2$Cl$_2$ and Li/SOCl$_2$ battery chemistries being the second best, followed by the Li/MnO$_2$ and Li/SVO batteries in third and fourth place, respectively. However, as indicated, the internal resistance characteristics of these batteries render them problematic if used alone in a defibrillator or ICD. The lowest energy density of all the above-listed battery chemistries is found in the lithium-ion rechargeable battery. The energy density level is so low that such batteries cannot realistically be used in implantable defibrillators and ICDs, notwithstanding their favorable internal resistance values.

The present invention overcomes the deficiencies of individual battery chemistries by combining two different battery chemistries wherein each battery is utilized in a manner that is optimally matched to its capabilities. An Li/CFx battery, Li/BrCl$_2$, Li/MnO, Li/SO$_2$Cl$_2$, Li/SOCl$_2$ or a Li/SVO battery can thus be chosen for the primary energy source (battery "A") because they provide superior total energy for a given battery volume. A lithium-ion secondary battery can be chosen as the energy source for the energy storage capacitors (battery "B") because it provides an internal resistance that is low and relatively stable, and is therefore capable of delivering the highest instantaneous power, providing the shortest charging time for the energy storage capacitors. The embodiments that are taught herein thus provide a clear advantage over single battery systems because each battery is used in an optimum fashion, yielding an implantable defibrillator or ICD with minimum capacitor charging time and maximum device service life.

The present invention is also superior with respect to precise end-of-life determination of the power source. In particular, a monitoring feature could be provided that monitors the voltage level of the primary battery "A." Over time, this voltage level may drop below the level necessary to trigger the voltage boost circuit. Monitoring the voltage level of the primary battery "A" would provide a warning that the secondary battery "B" is no longer being charged. However, if the secondary battery "B" is a lithium-ion cell, it will have a known capacity to deliver some number of defibrillatory pulses, say 50 pulses. It would thus be known that the defibrillator or ICD will work for this remaining number of pulses and steps can be taken to promptly replace the primary battery "A."

This present invention is also superior to the concepts disclosed in prior art that embodies multi-battery systems with respect to the management of energy transfer from a primary energy stage to a secondary energy stage. Whereas the cited prior art teaches the use of simple continuous trickle charging circuits or the use of voltage doubler circuits in conjunction with a second stage rechargeable battery, we teach the use of switch mode voltage boost/charge control circuit with feedback that provides recharging under controlled conditions to optimize the performance of the lithium-ion chemistry system utilized for the secondary battery "B."

Accordingly, a hybrid battery power source for implantable medical use has been disclosed and the objects of the invention have been achieved. It should, of course, be understood that the description and the drawings herein are merely illustrative, and it will be apparent that the various modifications, combinations and changes can be made of these structures disclosed in accordance with the invention. For example, it will be appreciated that conventional telemetry control circuitry could be used to control operation of the circuits shown in FIGS. 2, 4 and 5–6. Settings that could be adjusted in this fashion would include the voltage references Vthr_low and Vthr_high, as well as pulse generator duty cycle. It should be understood, therefore, that the invention is not to be in any way limited except in accordance with the spirit of the appended claims and their equivalents.

What is claimed is:

1. A hybrid battery power source for implantable medical use, comprising:
 a primary battery;
 a secondary battery connected to receive power from said primary battery;
 said secondary battery being adapted to power to an implantable medical device designed for high energy electrical stimulation of body tissue for therapeutic purposes; and
 a charge control circuit powered by said primary battery and including voltage reference and window comparator means for charging said secondary battery while limiting charge/discharge excursions thereof to control discharge capacity fade and internal resistance increase during service of said secondary battery.

2. A hybrid battery power source in accordance with claim 1 wherein said charge control circuit is a pulse output circuit adapted for variable pulse width or duty cycle control, thereby allowing it to operate over a range of voltages output by said primary battery.

3. A hybrid battery power source in accordance with claim 1 wherein said charge control circuit is adapted to charge said secondary battery over a charge/discharge excursion range that is below a maximum state-of-charge of said secondary battery.

4. A hybrid battery power source in accordance with claim 1 wherein said voltage reference and window comparator means includes first and second voltage comparators, said first voltage comparator being adapted to initiate charging when said secondary battery falls below a minimum voltage provided by a first voltage reference and said second voltage comparator being adapted to terminate charging when said secondary battery is charged to a maximum voltage provided by a second voltage reference.

5. A hybrid battery power source in accordance with claim 4 further including a pulse generator powered by said primary battery, said pulse generator being adapted to supply pulsatile power to said first and second voltage comparators and said first and second voltage references in order to conserve energy supplied by said primary battery to said charge control circuit.

6. A hybrid battery power source in accordance with claim 1 wherein said primary battery is selected from the group consisting of lithium-carbon monofluoride batteries, lithium-bromine chloride batteries, lithium-sulfuryl chloride batteries, lithium thionyl chloride batteries, lithium-manganese dioxide batteries, lithium-silver vanadium oxide batteries and lithium-iodide batteries, and wherein said secondary battery is selected from the group consisting of lithium-ion batteries.

7. A hybrid battery power source in accordance with claim 1 further including a voltage boost circuit that facilitates charging of said secondary battery at a voltage that is higher than a voltage output of said primary battery.

8. A hybrid battery power source in accordance with claim 7 wherein said voltage boost circuit comprises one of an inductive element or flyback transformer.

9. A hybrid battery power source in accordance with claim 7 wherein said voltage boost circuit comprises a capacitive charge storage device.

10. A hybrid battery power source in accordance with claim 9 wherein said voltage boost circuit is adapted to produce charging pulses of sufficiently short duration to reduce the discharge rate of said primary battery to a level that is compatible with the maximum discharge current capacity thereof.

11. An implantable medical device for high energy electrical stimulation of body tissue for therapeutic purposes, comprising:
 a pair of electrical contacts adapted to provide electrical stimulation to body tissue;
 energy storage means adapted to provide electrical energy to said electrical contacts;
 switching means adapted to periodically interconnect said energy storage means to said electrical contacts; and
 a hybrid battery power source adapted to provide power to said energy storage means and including:
 a primary battery;
 a secondary battery connected to receive power from said primary battery and to provide power to said energy storage means; and
 a charge control circuit powered by said primary battery and including voltage reference and window comparator means for charging said secondary battery while limiting charge/discharge excursions thereof to control discharge capacity fade and internal resistance increase during service of said secondary battery.

12. An implantable medical device in accordance with claim 11 wherein said charge control circuit is a pulse output circuit adapted for variable pulse width or duty cycle control, thereby allowing it to operate over a range of voltages output by said primary battery.

13. An implantable medical device in accordance with claim 11 wherein said charge control circuit is adapted to charge said secondary battery over a charge/discharge excursion range that is below a maximum state-of-charge of said secondary battery.

14. An implantable medical device in accordance with claim 11 wherein said voltage reference and window comparator means includes first and second voltage comparators, said first voltage comparator being adapted to initiate charging when said secondary battery falls below a minimum voltage provided by a first voltage reference and said second voltage comparator being adapted to terminate charging when said secondary battery is charged to a maximum voltage provided by a second voltage reference.

15. An implantable medical device in accordance with claim 14 further including a pulse generator powered by said primary battery, said pulse generator being adapted to supply pulsatile power to said first and second voltage comparators and said first and second voltage references in order to conserve energy supplied by said primary battery to said charge control circuit.

16. An implantable medical device in accordance with claim 11 wherein said primary battery is selected from the group consisting of lithium-carbon monofluoride batteries, lithium-bromine chloride batteries, lithium-sulfuryl chloride batteries, lithium thionyl chloride batteries, lithium-manganese dioxide batteries, lithium-silver vanadium oxide batteries and lithium-iodide batteries, and wherein said secondary battery is selected from the group consisting of lithium-ion batteries.

17. An implantable medical device in accordance with claim 11 further including a voltage boost circuit that facilitates charging of said secondary battery at a voltage that is higher than a voltage output of said primary battery.

18. An implantable medical device in accordance with claim 17 wherein said voltage boost circuit comprises one of an inductive element or flyback transformer.

19. An implantable medical device in accordance with claim 17 wherein said voltage boost circuit comprises a capacitive charge storage device.

20. An implantable medical device in accordance with claim 19 wherein said voltage boost circuit is adapted to produce charging pulses of sufficiently short duration to reduce the discharge rate of said primary battery to a level that is compatible with the maximum discharge current capacity thereof.

21. A method for powering an implantable medical device designed for high energy electrical stimulation of body tissue for therapeutic purposes, comprising:
providing a primary battery;
providing a secondary battery and connecting it to receive power from said primary power battery;
connecting said secondary battery to power said implantable medical device;
periodically monitoring the charge state of said secondary battery; and
periodically charging said secondary battery by way of said primary battery while limiting charge/discharge excursions of said secondary battery to control discharge capacity fade and internal resistance increase during service of said secondary battery.

22. A method in accordance with claim 21 wherein said charging is performed under variable pulse width or duty cycle control over a range of voltages output by said primary battery.

23. A method in accordance with claim 21 wherein said charging comprises charging said secondary battery over a charge/discharge excursion range that is below a maximum state-of-charge of said secondary battery.

24. A method in accordance with claim 21 wherein said monitoring comprises a first periodic comparison to initiate charging when said secondary battery falls below a minimum voltage and a second periodic comparison to terminate charging when said secondary battery is charged to a maximum voltage.

25. A method in accordance with claim 24 wherein said first and second comparisons are performed using pulsatile energy delivered by said primary battery in order to conserve energy supplied by said primary battery for said first and second comparisons.

26. A method in accordance with claim 21 wherein said primary battery is selected from the group consisting of lithium-carbon monofluoride batteries, lithium-bromine chloride batteries, lithium-sulfuryl chloride batteries, lithium thionyl chloride batteries, lithium-manganese dioxide batteries, lithium-silver vanadium oxide batteries and lithium-iodide batteries, and wherein said secondary battery is selected from the group consisting of lithium-ion batteries.

27. A method in accordance with claim 21 further including voltage boosting in order to charge said secondary battery at a voltage that is higher than a voltage output of said primary battery.

28. A method in accordance with claim 27 wherein said voltage boosting comprises inductive voltage boosting.

29. A method in accordance with claim 27 wherein said voltage boosting comprises capacitive voltage boosting.

30. A method in accordance with claim 29 wherein said voltage boosting comprises producing charging pulses of sufficiently short duration to reduce the discharge rate of said primary battery to a level that is compatible with the maximum discharge current capacity thereof.

* * * * *